United States Patent [19]

Akkara et al.

[11] Patent Number: 5,169,554

[45] Date of Patent: Dec. 8, 1992

[54] ENZYME DETERGENT FORMULATION AND METHODS OF DETOXIFYING TOXIC ORGANOPHOSPHOROUS ACID COMPOUNDS

[75] Inventors: Joseph A. Akkara, Holliston; David L. Kaplan, Stow; Arthur M. Kaplan, Newton, all of Mass.

[73] Assignee: The United States of America as represented by the Secretary of the Army, Washington, D.C.

[21] Appl. No.: 417,614

[22] Filed: Oct. 4, 1989

[51] Int. Cl.$^5$ .................... C11D 17/00; C11D 7/06; C11D 7/12
[52] U.S. Cl. .................... 252/174.12; 252/156; 252/173; 252/174.23; 252/174.24; 252/DIG. 12; 252/DIG. 14; 435/264
[58] Field of Search .................... 252/156, 173, 174.12, 252/174.23, 174.24, DIG. 12, DIG. 14; 435/264

[56] References Cited

U.S. PATENT DOCUMENTS

| | | | |
|---|---|---|---|
| 3,649,454 | 3/1972 | Masao Isono et al. | 252/174.12 |
| 4,865,983 | 9/1989 | Durham | 252/174.12 |
| 4,883,757 | 11/1989 | Gutnick et al. | 252/351 |

FOREIGN PATENT DOCUMENTS

0273125  6/1988  European Pat. Off.

OTHER PUBLICATIONS

Hoskin et al., *Two Enzymes for the Detotification of Organophosphorous Compounds*, Fundamentals of Applied Toxicology, 4(2, Pt. 2), 165–172.

Moss et al., *Efficient Catalytic Cleavage of Reactive Phosphates by o-Iodosobenzoate Functionalized Surfactant*, J. American Chemical Society, 1986, 108, 788–793.

"Soman Hydrolysis and Detoxication by a Thermophilic Bacterial Enzyme", F. Hoskin et al., Enzymes Hydrolysing Organophosphorus Compounds, pp. 53–64, (1989).

"Soman-Hydrolyzing and -Detoxifying Properties of an Enzyme from a Thermophilic Bacterium", G. Chettur et al., Fundamental and Applied Technology, II, pp. 373–380, (1988).

Benschop et al., Fundamental and Applied Toxicology, vol. 1, pp. 177–182 (1981).

Benschop et al., Journal of American Chemical Society, vol. 103, pp. 4260–4262 (1981).

*Primary Examiner*—A. Lionel Clingman
*Assistant Examiner*—William S. Parks
*Attorney, Agent, or Firm*—Richard J. Donahue; Lawrence E. Labadini

[57] ABSTRACT

An enzyme detergent composition capable of detoxifying G-agents and other OPA chemicals comprises a laundry detergent and an enzymatic cell free extract from *E. coli*, the composition having a pH of about 6.5 to 10 in water.

A method of hydrolyzing a hydrolyzable compound comprises contacting compound with an amount of an aqueous suspension of the enzyme detergent composition of the invention under conditions affective to attain the desired affect.

A method of cleaning and detoxifying a product comprising a hydrolyzable compound comprises contacting the product with an amount of an aqueous suspension of the enzyme detergent composition of the invention under conditions capable of attaining the desired affect, and rinsing the product.

6 Claims, 2 Drawing Sheets

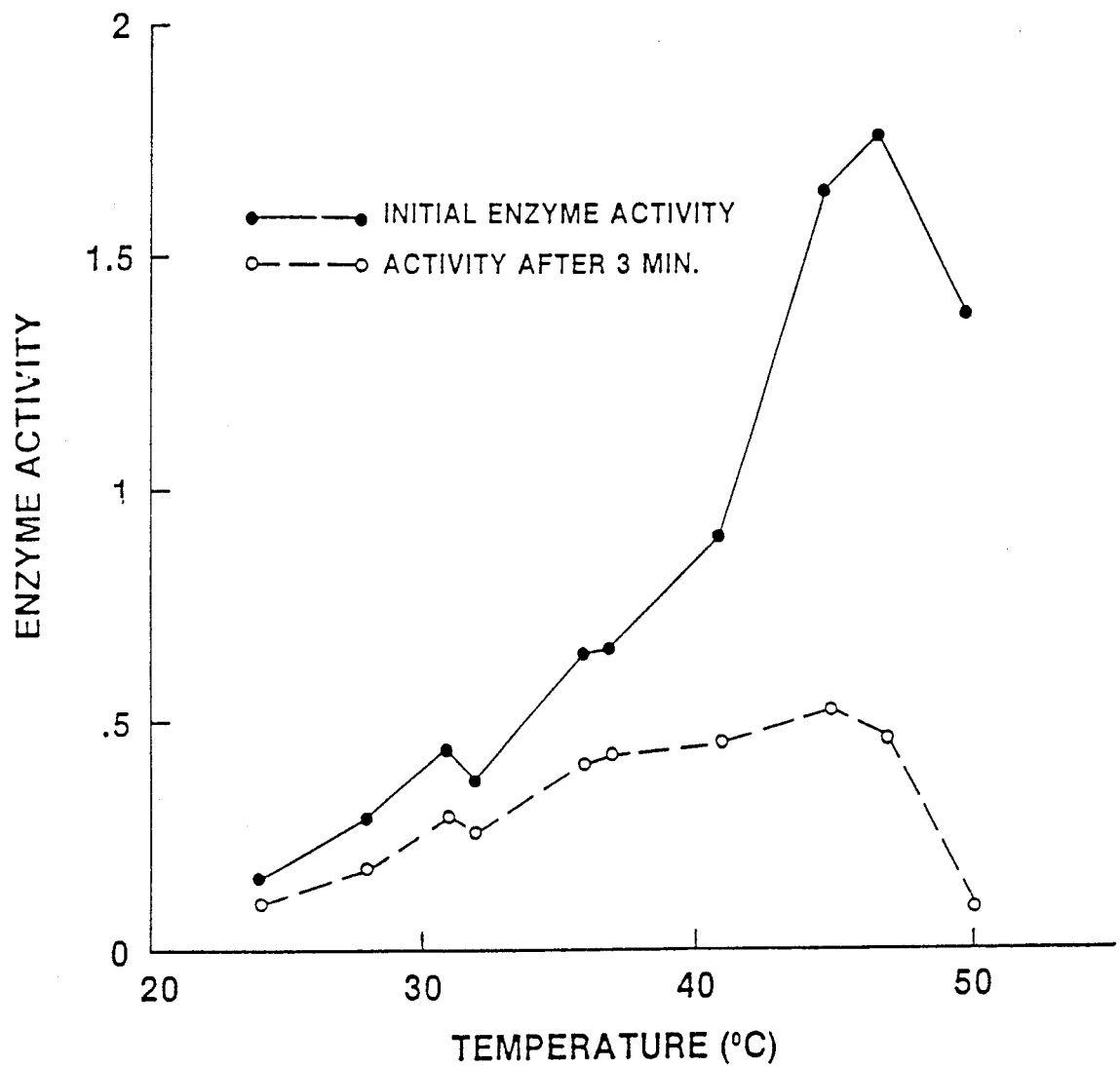
FIGURE 1. TEMP. PROFILE OF *E. COLI* ENZYME

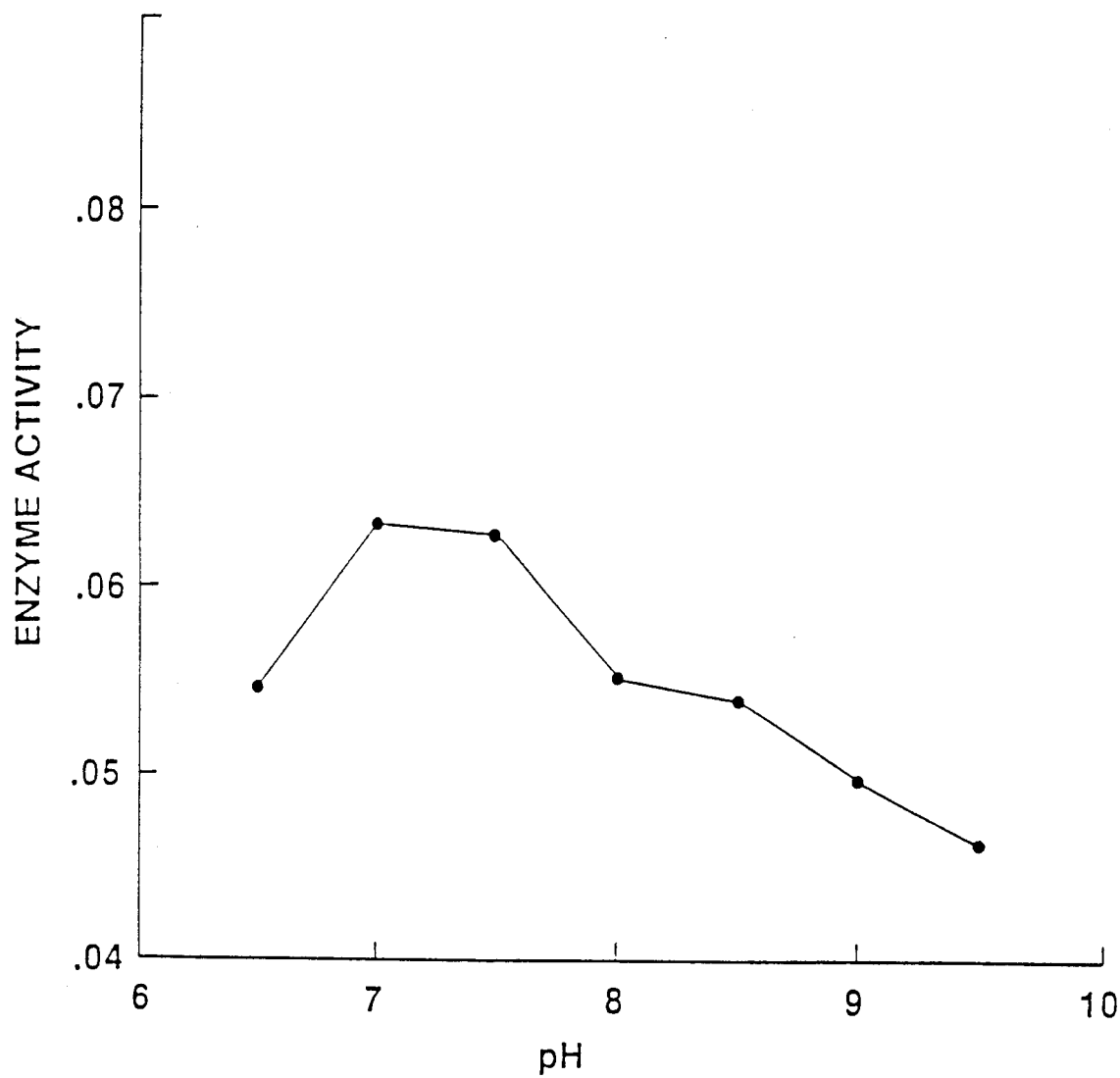
FIGURE 2. pH OPTIMUM OF *E. COLI* ENZYME ACTIVITY

ENZYME DETERGENT FORMULATION AND METHODS OF DETOXIFYING TOXIC ORGANOPHOSPHOROUS ACID COMPOUNDS The invention described herein may be manufactured, used and licensed by or for the government for government purposes without the payment of any royalty thereon.

TECHNICAL FIELD

This invention relates to an enzyme detergent formulation which is capable of cleaning and decontaminating toxic organophosphorus acid compounds and their salts from clothing and other articles. This is done under mild conditions of pH and temperature which will not adversely effect the functional properties of clothing and other articles.

BACKGROUND ART

Many laundry detergents available in the market contain enzymes to facilitate the removal of protein, carbohydrate and lipid based stains and soils from clothing under mild laundering conditions.

Toxic organophosphorus acid compounds and other salts can be encountered in industrial, agricultural and military operations. Such toxic materials can be removed and detoxified by the application of harsh chemicals or elevated temperatures, either of which may degrade the articles being detoxified.

Thus, a need exists for a detergent formulation capable of rapid detoxification of toxic organophosphorus acid compounds and their salts under mild conditions which will not have a harmful effect on articles so treated.

DISCLOSURE OF THE INVENTION

This invention relates to an enzyme detergent composition capable of detoxifying toxic organophosphorus acid compounds and salts thereof comprising
a detergent formulation; and
an enzymatic cell free extract from *E. coli*, the composition having a pH of about 5 to 9.5 in water.

This invention also relates to a method of hydrolyzing and detoxifying toxic compounds of organophosphorus acids and their salts comprising contacting said compounds with an amount of an aqueous suspension of the enzyme detergent composition described above under conditions effective to attain said hydrolysis and detoxification.

Also part of this invention is a method of cleaning and detoxifying a product contaminated with at least one toxic compound selected from organophosphorus acids and their salts, comprising
contacting the product with an amount of the aqueous suspension of the enzyme detergent composition of this invention under conditions capable of attaining the desired affect; and
rinsing the product.

A more complete appreciation of the invention and many of the attendant advantages thereof will be readily perceived as the same becomes better understood by reference to the following detailed description when considered in connection with the accompanying figures.

BRIEF DESCRIPTION OF DRAWINGS

FIG. 1 depicts the variation of the *E. coli* enzyme activity with temperature both at an initial time and after three minutes of contact.

FIG. 2 depicts the variation of the *E. coli* enzyme activity with the pH of the aqueous medium.

Other objects, advantages and features of the present invention will become apparent to those skilled in the art from the following discussion.

BEST MODE FOR CARRYING OUT THE INVENTION

The present invention arose from a desire by the inventors to improve on prior art detergent formulations to provide an enzyme detergent preparation capable of rapid detoxification of clothing and other articles contaminated with toxic organophosphorus acid compounds and their salts under mild conditions which would not adversely effect the functional properties of contaminated clothing and other articles.

Toxic organophosphorus acids and their salts (OPA) include organoflurophosphonates (warfare nerve agent, called G-agents such as soman), organophosphonates, organophosphinates and organophosphates (pesticides such as parathion, paroxon and methyl parathion).

An enzyme detergent formulation has been developed comprising commercially available detergent and an enzyme from the bacterium *Escherichia coli*. The hydrolysis of G-agents such as soman was increased up to about 16-fold and more with the present enzyme detergent formulation over that observed with the detergent formulation alone at a pH 9.5.

Soman, hydrolyzed at pH 9.5 and 40° C., was detoxified up to 91% in 10 minutes in the presence of the enzyme detergent formulation of the invention. The cleaning and decontaminating conditions required for this enzyme detergent formulation are very mild, which preserve the functional finishes on the clothing on other articles being cleaned and decontaminated.

Moreover, this formulation is compatible with current Army field laundry equipment. This enzyme detergent formulation can be used to decontaminate OPA chemicals, such as G-agents, in laundry applications in place of super Tropical Bleach presently recommended by the Army Field Manual.

A purpose of this invention is to provide a detergent formulation that not only launders or cleans, but also decontaminates soiled clothing or other articles contaminated with, e.g., G-agents. Under normal laundry conditions G-agents are hydrolyzed slowly. The rate of hydrolysis or half-life of soman (pinacolyl methylphosphonofloridate) at 25° C. and at pH 10 is 60 hours.

It is critical to catalytically destroy the agent at a faster rate, while at the same time cleaning soiled clothing and equipment under mild conditions and using equipment available in the field. The decontaminating enzyme formulation provided therein extends the life cycle of both field clothing and equipment, and reduces logistic burdens.

The activities of decontaminating enzyme detergent formulations against OPA chemicals such as G-agents and G-agent surrogates have been determined at different pHs, temperatures, and with different substrates and inhibitors. The activity of the enzyme itself against G-agent and G-agent surrogates has also been studied in the presence of different detergent components. Live agent testing with soman using enzyme detergent formulations and a non-enzymatic catalyst containing detergent formulations involved both the hydrolysis and the detoxification of soman.

This invention provides an enzyme detergent composition which is capable of detoxifying G-agents, the composition comprising a laundry detergent; and an enzymatic cell free extract from *E. coli,* the composition having a pH of about 5 to 9.5 in water.

A variety of laundry detergents may be utilized in the present composition. Examples of laundry detergents are ionic and non-ionic types of detergents such as alkali detergents, type II laundry detergents, linear alkyl sulfonate, Tide "New Liquid" and type I non-ionic detergents. However, other detergents can also be utilized. Particularly preferred are laundry detergents such as alkali detergent and laundry detergent type II. The amount of laundry detergent present in the composition is typically about 0.01 wt % to 10.0 wt. %, and more preferably about 0.01 wt % to 50 wt. %. However, other amounts are also possible.

The enzymatic cell free extract from *E. coli* is typically present in an amount of about 1.0 to 20 of the composition, and more preferably 2.0 to 10 volume percent of the composition. However, other amounts may also be utilized.

The enzyme detergent formulation of this invention may also comprise a non-enzymatic catalyst, such as iodosobenzoate. Typically, this catalyst compound is present in an amount of about 0.001 to 10 wt %, and more preferably about 0.001 to 5 wt % of the composition. However, other amounts are also suitable The cell free extract may be obtained by sonicating *E. coli* cells and then centrifuging the disrupted cells thus obtained. These are technologies which are standard in the art.

In a particularly preferred embodiment of the enzyme detergent formulation described herein the enzymatic cell free extract is obtained from *E. coli* having an ATCC Accession No. 25922. A still more preferred embodiment is that comprising the purified enzyme obtained from this microorganism.

The enzyme can be obtained from the *E. coli* microorganism as follows. Escherichia coli (ATCC 25922 may be grown in, e.g., trypticase soy broth (about 3%) and incubated for about 18–40 hours at about 37° C. The cells may then be separated from the medium, washed once in a buffer containing, e.g., about 400 mM sodium chloride, about 40 mM potassium chloride and about 5 mM bistris at a pH about 7.2. The washed cells may then be resuspended in the same buffer to give an about 10% (w/v) suspension. These bacterial cells may be broken up by ultrasonic oscillator at about 4° C., for, e.g., about 5 minutes. The output from the sonifier may be pulsed and the output interrupted to maintain the temperature of the cell suspension at about 4° C. The disrupted cell suspension may be centrifuged for about 30 minutes at about 4° C. at 30,000x g, and the supernatant used as the source of *E. coli* enzyme (Akkara, J. A., Kaplan, D. L., and Kaplan, A. M., "Enzyme Formulation for Laundering and Decontaminating Chemically Contained Clothing", Technical Report, Natick TR-88/014L, U.S. Army Natick Research, Development and Engineering Center, Natick, MA (1988)).

In another preferred embodiment the enzymatic cell free extract is provided in freeze dried form. The manner in which the freeze dried product is processed is known in the art and need not be described herein in further detail.

Another particularly preferred embodiment of the composition further comprises a manganese compound such as manganese chloride. However, other manganese salts may also be utilized. Typically, the manganese compound is present in an amount of about 0.001 to 10 wt %, and more preferably about 0.1 to 5 wt % of the composition.

Also part of this invention is the method of hydrolyzing an OPA chemical comprising contacting said compound with an amount of an aqueous suspension of the enzyme detergent composition described herein under conditions effective to attain the desired effect.

Typically, the method may be conducted at a temperature of about 20° to 50° C., and more preferably about 30° to 45° C. However, other temperature ranges within the broader range may also be utilized.

The above method may be preferably practiced preserving the pH at about 6.5 to 10.0, and more preferably about 7 to 9.5.

Also part of this invention is a method of cleaning and detoxifying a product contaminated with an OPA chemical, comprises contacting the product with an amount of an aqueous suspension of the enzyme detergent formulation described herein under conditions capable of attaining the desired effect; and rinsing the product.

Typically, the contacting step is conducted at a temperature of about 20° to 50° C., and more preferably about 25° to 45° C. The pH utilized for the practice of the contacting step is preferably about 6.5 to 8, and more preferably about 7 to 7.5. Under these conditions OPA chemicals may be detoxified while the product is cleaned.

Having now generally described this invention, the same will be better understood by reference to certain specific examples, which are included herein for purposes of illustration only and are not intended to be limiting of the invention or any embodiment thereof, unless so specified.

EXAMPLES

EXAMPLE 1

Culture of *Escherichia coli*

*E. coli* ATCC No. 25922 was grown in trypticase soy broth (3%) (Difco Laboratories, Detroit, Mich.) and incubated for about 18 to 40 hours at 37°2 C. The cells were harvested, washed once with buffer containing 400 nM sodium chloride, 40 mM potassium chloride and 5 mM bis tris at pH 7.2.

The bacteria were resuspended in the above buffer to give 10% (w/v) suspension.

EXAMPLE 2

Preparation of Cell free Extract

The bacterial cell suspension prepared above was ultrasonically disrupted by a Branson sonifier.$^R$ at 4° C., for 5 minutes, using a microtip and with a pulsed input at 40% duty cycle and output control setting at 4 (Model #350, Branson Sonic Power Co., Danbury, Conn.).

The pulsed input from the sonifier was for 30 seconds followed by one minute cooling in between the sonification. This cycle was repeated until the total sonification time was 5 minutes. A cell free extract was prepared from the disrupted cell suspension, after centrifugation at 30,000x g for 30 minutes at 4° C.

The cell free crude extract was used for the determination of the enzyme activity, including G-agent hydrolysis and detoxification studies.

EXAMPLE 3

Chemicals

The following chemicals were purchased from commercial sources: diisopropyl fluorophosphonate (DFP), bis para-nitrophenyl phosphate (bis pNPP), para-nitrophenyl acetate, parathion, methyl parathion, paraoxon, 4 nitrophenyl ethyl (phenyl) phosphinate and iodosobenoic acid (IB). Soman (GD) used in the agent testing with detergent formulation was supplied by the Illinois Institute of Technology Research Institute (IITRI)

EXAMPLE 4

Detergents

Alkali (CID-A-A-876), (U.S. Government Printing Office, Customer Item Description, Alkali, Laundry CID-A-A-876, General Services Administration, Washington, D.C. (1980)), Laundry Detergent, Type II (P-D-245-E), non-ionic Detergent Type I (MIL-D-16791-F), Tide "New Liquid" (Procter and Gamble, Cincinnati, Ohio) and Linear Alkyl Sulfonate (Soap and Detergent Association, N.Y., N.Y.) were obtained from commercial sources.

EXAMPLE 5

Enzymes

Commercial hydrolytic enzymes neutrase 1.5 G, esperase 4.0 T, alcalase 2.0 T, savinase 8.0 SL, and Nue #1, 6.0 S were obtained from Novo Laboratories, Wilton, Conn., and stored at 4° C. These enzymes were in slurry (SL), granulated (G,T),;or powder (S) form.

EXAMPLE 6

Protein Determination

The protein concentration of the cell free extract of *E. coli* was determined by Bio Rad Protein Assay Kit (Bio Rad, Richmond, Cal.) using Coomassie Brilliant Blue G-250 dye.

EXAMPLE 7

Fluoride Determination

A fluoride specific electrode (Orion Research, Cambridge, Mass.) was connected with a Fisher Titrator (Model #750, Medford, Mass.) with strip chart (Hitachi Recorder #056-1001) to determine the rate of hydrolysis of DFP and soman by determining the fluoride that is released.

EXAMPLE 8

Enzyme Assay

A colorimetric method for the determination of the enzyme activity involved the measurement of paranitrophenol formed at 405 nm in the presence of manganese chloride.

DFP and soman hydrolysis by the catalysts was followed by the measurement of the fluoride released using the fluoride specific electrode. The electrode was calibrated with detergent solutions (without enzyme and iodosobenzoate) containing known amounts of fluoride before the catalytic activity was determined.

The activity was measured at room temperature unless otherwise indicated.

EXAMPLE 9

Agent Testing

Soman testing with enzyme/iodosobenzoate detergent formulations was carried out. The agent testing included both the hydrolysis and the detoxification of the agent.

The hydrolysis of soman was followed by measuring fluoride released by the fluoride specific electrode. The detoxification of soman by the enzyme/iodosobenzoate detergent formulations was calculated from the second order inhibition rate constant by the Ellman color reaction using eel acetylcholinesterase enzyme, with acetylthiocholine bromide as the substrate and dithiobisnitrobenzoic acid as the indicator (Ellman, G. L., Courtney, K. D., Andres, V. Jr., and Featherstone, R. M., "A New Rapid Determination of Acetylcholinesterase Activity" Biochem. Pharmacol. 7:88-95 (1961)).

EXAMPLE 10

Activity of *E. coli* Enzyme

FIG. 1 shows variation of the activity of the *E. coli* enzyme with temperature, when bis para-nitrophenyl phosphate (bis pNPP) was used as the substrate. The activity of the enzyme increased with the increase in incubation temperature up to 45° C., above which the enzyme was deactivated very rapidly. The activity reported is the net activity due to the enzyme after subtracting the activity without the enzyme.

The second plot in FIG. 1 gives the rate of the reaction after three minutes into the reaction. The three minute plot clearly indicates that the rate of the reaction dropped to about 75% of the initial rate at 45° C. The pH optimum of the *E. coli* enzyme is given in FIG. 2, when bis pNPP was used as the substrate. It appears from the curve that the enzyme may have two pH optima, one at 7 to 7.5, and the second one near pH 8.5.

EXAMPLE 11

Substrate Specificity of *E. coli* Enzyme

The substrate specificity of the *E. coli* enzyme was determined with different phosphate esters. Paranitrophenyl acetate and bis pNPP had comparable activities. However, with other substrates such as: parathion, methyl parathion and paraoxon, the enzyme activity was much lower as can be seen in Table 1.

TABLE 1

| Substrate Specificity of *E. coli* Enzyme | |
|---|---|
| Substrate | Specific Activity |
| bis para Nitrophenyl phosphate | 0.128 |
| para-Nitrophenyl acetate | 0.130 |
| Parathion | 0.042 |
| Methyl parathion | 0.035 |
| Paraoxon | 0.022 |

*The activity of enzyme was measured at 37° C. at pH 7.2. The units of activity are μ moles of paranitrophenol formed/min./mg protein.

Table 2 below shows the rate of hydrolysis of DFP at room temperature in the presence of different detergent formulations or detergent components. The net hydrolysis was much higher at pH 9.5 and in presence of detergent.

TABLE 2

Hydrolysis of DFP with *E. coli* Extract[a,b]

| Hydrolyzing Medium | pH 7.5 | pH 8.5 | pH 9.5 |
|---|---|---|---|
| Alkali[c] | 0.02 | 0.05 | 0.18 |
| Tide[d] | 0.008 | 0.0 | 0.0 |
| Nonionic Detergent[e] | 0.0 | 0.005 | 0.03 |
| bis Tris Propane | 0.04 | 0.01 | 0.04 |
| Glycine-NaOH | nd[f] | nd[f] | 0.05 |

[a]Hydrolysis of DFP is followed by measuring the fluoride released with a fluoride specific electrode. The enzyme activity was measured as μ moles of fluoride released/minute/mL of *E. coli* extract.
[b]One milliliter of *E. coli* extract contained 14.4 mg protein.
[c]Alkali Laundry CID-A-A-876, General Services Administration, Washington, D.C. (1980).
[d]Tide "New Liquid" (Procter and Gamble, Ohio).
[e]Non-ionic Detergent Type I. Military Specification, Detergent, General Purpose (Liquid, Nonionic), MIL-D-16791F.
[f]No data.

EXAMPLE 12

Further Addition of Iodosobenzoate

Moss et al have shown that iodosobenzoic acid catalytically hydrolyzed phospho-esters (Moss, R. A., Kim, K. Y., and Swarup, S., "Efficient Catalytic Cleavage of Reactive Phosphates by an O-Iodosobenzoate Functionalized Surfactant" J. Amer. Chem. Soc., 108:788-783 (1986); Moss, R. A., and Swarup, S., "Surface Specific Phosphate Cleavage of a Substrate Functionalized Vesicular Surfactant" J. Amer. Chem. Soc., 108:5341-5342 (1986); Moss, R. A., Hendrickson, T. F., and Bizziggotti, G. O., "The Esterolytic Chemistry of a Vesicular Thiocholine Surfactant" J. Amer. Chem. Soc., 108:5520-5527 (1986)). The catalytic effects of iodosobenzoate in the presence of detergent formulations or detergent components were determined and the results are shown in Table 3 below. The formulation contains 0.0075 wt/volume of the iodosobenzoate.

TABLE 3

Hydrolysis of DFP with Iodosobenzoate[a]

| Hydrolyzing | pH 7.5 | pH 8.5 | pH 9.5 |
|---|---|---|---|
| Alkali[b] | 0.06 | 0.16 | 0.13 |
| Nonionic Detergent[c] | 0.08 | 0.006 | 0.08 |
| "Sea water" synthetic[d] | nd[f] | 0.02 | nd |
| Sea water[e] | nd | 0.03 | nd |
| bis Tris Propane | 0.03 | 0.05 | 0.04 |
| Glycine-NaOH | nd | nd | 0.05 |

[a]The hydrolysis of DFP was followed by measuring the fluoride released with a fluoride specific electrode. The activity was measured as μ moles of fluoride released/minute/mg of iodsobenzoate.
[b]Alkali Laundry CID-A-A-876, General Services Administration, Washington, D.C. (1980).
[c]Non-ionic Detergent Type I. Military Specification, Detergent, General Purpose (Liquid, Non-ionic), MIL-D-16791F.
[d]Instant Ocean, Aquarium System, 8141 Tyler Blvd., Mentor, OH.
[e]Collected from Narragansett Bay, RI.
[f]No data.

DFP was hydrolyzed at about the same rate at pHs 8.5 and 9.5 in the presence of alkali. The hydrolysis of DFP by iodosobenzoate in the presence of "Synthetic Sea Water" (Instant Ocean Aquarium System, Mention, Oh.) or sea water (collected from Naragansett Bay, R.I.) at pH 8.5 showed lower activities. All formulations contain 0.0075 wt/volume of iodosobenzoate.

EXAMPLE 13

Hydrolysis of Soman with Iodosobenzoate and Detergent Type II and Alkali or Non-ionic Detergent Type I Table 4 below presents the results of the hydrolysis of soman with iodosobenzoate, at 30° C. and 40° C., and in the presence of various detergents.

With iodosobenzoate, the rate of hydrolysis of soman was higher at 40° C. than at 30° C. at pH 9.5 with either alkali or laundry detergent Type II. The hydrolysis of soman was lower in the presence of non-ionic detergent. Each formulation contains 0.075 wt/volume of iodosobenzoate.

TABLE 4

Hydrolysis of Soman with Iodosobenzoate[a]

| Hydrolyzing Medium | pH 7.5 | pH 8.5 | pH 9.5 |
|---|---|---|---|
| I. 30° C. | | | |
| Alkali[b] | 1.24 | 1.08 | 1.78 |
| Detergent[c] | 1.25 | 1.56 | 1.64 |
| Nonionic Detergent[d] | 0.97 | 0.74 | 0.73 |
| II. 40° C. | | | |
| Alkali[b] | 2.36 | 1.89 | 3.63 |
| Detergent[c] | 2.13 | 2.45 | 2.91 |
| Nonionic Detergent[d] | 1.45 | 1.20 | 1.19 |

[a]Hydrolysis of Soman is followed by measuring the fluoride released with a fluoride specific electrode. The activity was measured as μ moles of fluoride released/minute/mg of iodsobenzoate.
[b]Alkali Laundry CID-A-A-876, General Services Administration, Washington, D.C. (1980).
[c]Laundry Detergent Type II. Federal Specification Detergent, Laundry and Hand Washing (Granular), P-D-245E.
[d]Non-ionic Detergent Type I. Military Specification, Detergent, General Purpose (Liquid, Nonionic), MIL-D-16791F.

EXAMPLE 14

Hydrolysis Detoxification of Soman with Iodosobenzoate and Detergent Type II and Alkali Table 5 below gives the data on the hydrolysis and detoxification of soman by iodosobenzoate in presence of alkali and laundry detergent type II at 40° C. and at pH 9.5.

TABLE 5

Hydrolysis and Detoxification of Soman by Iodosobenzoate[a]

| | Percent Hydrolysis | Percent Detoxification |
|---|---|---|
| I. Buffer[b] | 20.3 | 18.3 |
| Alkali[c] | 22.2 | 33.4 |
| Alkali[c] + Iodosobenzoate | 41.7 | 58.3 |
| II. Buffer[b] | 12.9 | 15.4 |
| Detergent[d] | 12.9 | 21.1 |
| Detergent[d] + Iodosobensoate | 36.1 | 37.4 |

[a]Hydrolysis of soman is followed by measuring the fluoride released with the ion specific electrode. Detoxification of soman was determined by measuring the inhibition of acetylcholinesterase enzyme.
[b]Buffer: 0.05M glycine-NaOH pH 9.5.
[c]Alkali, Laundry CID-A-A-876.
[d]Laundry detergent type II. Federal Specification, Detergent, Laundry and Hand Washing (Granular), P-D-245E.

EXAMPLE 15

Detoxification Studies

The detoxification studies were carried out by determining the inhibition of eel acetyl cholinesterase enzyme (Ellman, G. L., Courtney, K. D., Andres, J. Jr., and Featherstone, R. M., "A New Rapid Determination of Acetylcohlinesterase Activity " Biochem. Phramacol. 7:88-95 (1961)). The data indicate that there was significant hydrolysis and detoxification of soman in presence of alkali. Both hydrolysis and detoxification were increased by the presence of iodosobenzoate in the detergent formulations. Detoxification was higher than hydrolysis in the presence of alkali and alkali in the presence of iodosobenzoate.

EXAMPLE 16

Hydrolysis with Commercially Available Enzymes.

Commercially available hydrolytic enzymes were also evaluated for hydrolysis of bis pNPP and DFP. Table 6 below gives the results obtained with a number of these enzymes purchased ;from Novo Laboratories, Conn.

TABLE 6

Phosphodiesterase Activity with Commercial Enzymes

| Enzyme | Enzyme Activity[a] |
|---|---|
| Neutrase 1.5 G[b] | 3.0 |
| Esperase 4.0 T[c] | 0.09 |
| Alcalase 2.0 T[d] | 0.0 |
| Savinase 8.0 SL[e] | 0.07 |
| Nue #1, 6.0 S[f] | 0.09 |

[a]The enzyme activity is measured by the hydrolysis of bis para-nitrophenyl phosphate at 405 nm and at room temperature. The activity of the enzyme was measured as μ moles of para-nitrophenol formed/minute/mg enzyme × $10^{-3}$.
[b]Batch #PW 20508, Novo Laboratories, CT.
[c]Batch #PE 80280, Novo Laboratories, CT.
[d]Batch #PM 81601, Novo Laboratories, CT.
[e]Batch #PB 60004, Novo Laboratories, CT.
[f]Batch #PN 20761, Novo Laboratories, CT.

Neutrase 1.5 G was the most active with bis pNPP as the substrate. Neutrase 1.5 G was further evaluated with DFP as the substrate at different pHs and in the presence of Alkali as shown in Table 7 below.

TABLE 7

Hydrolysis of DFP with Neutrase Enzyme[a,b]

| Hydrolyzing Medium | pH 7.5 | pH 8.5 | pH 9.5 |
|---|---|---|---|
| Alkali[c] | 0.0 | 0.0 | 0.1 |
| bis Tris Propane | 0.0 | 0.0 | 0.03 |

[a]Hydrolysis of DFP is followed by measuring the fluoride released with a fluoride specific electrode. The activity was measured as μ moles of fluoride released/-minute/mg of enzyme.
[b]Neutrase 1.5 G Batch #PW 20508, Novo Laboratories, CT.
[c]Alkali, Laundry CID-A-A-876.

The hydrolytic activity of this enzyme was 0.1 umole per minute per milligram of Neutrase 1.5 G at pH 9.5. The hydrolysis and detoxification studies of soman by neutrase in the presence of alkali and laundry detergent type II also indicates that there was substantially no catalytic breakdown of soman by this enzyme at pH 9.5 and at 40° C.

EXAMPLE 17

Hydrolysis of Soman by *E. coli* Enzyme in the presence of Alkali, Laundry Detergent Type II or Non-Ionic Detergent at different pHs.

Table 8 below gives the results of the agent testing carried out using the *E. coli* extract in presence of alkali, laundry detergent type II, or non-ionic detergent at 30° C. and at different pHs.

TABLE 8

Hydrolysis of Soman with *E. coli* Enzyme at 30° C.[a]

| Hydrolyzing Medium | pH 7.5 | pH 8.5 | pH 9.5 |
|---|---|---|---|
| Alkali[b] | 1.98 | 2.01 | 2.00 |
| Detergent[c] | 1.88 | 2.03 | 1.90 |
| Non-ionic Detergent[d] | 1.50 | 1.49 | 1.63 |

[a]Hydrolysis of Soman is followed by measuring the fluoride released with the ion specific electrode. The activity of the enzyme was expressed as μ moles of fluoride released/minute/mL of enzyme.
[b]Alkali, Laundry CID-A-A-876.
[c]Laundry Detergent Type II, Federal Specification, Detergent, Laundry and Hand Washing (Granular), P-D-245E.
[d]Non-ionic Detergent Type I, Military Specification, Detergent, General Purpose (Liquid, Nonionic), MIL-D-16791F.

The rates given in Table 8 above are the net activities due to the enzyme.

The hydrolysis reaction was followed for 10 minutes after the electrode was stabilized with the detergent formulation (without the catalyst).

EXAMPLE 18

Hydrolysis of Soman with the *E. coli* Enzyme—Detergent at Different pHs

Table 9 below shows data obtained for the hydrolysis of soman with *E. coli* enzyme detergent formulation at 40° C. incubation and at different pHs.

TABLE 9

Hydrolysis of Soman with *E. coli* Enzyme at 40° C.[a]

| Hydrolyzing Medium | pH 7.5 | pH 8.5 | pH 9.5 |
|---|---|---|---|
| Alkali[b] | 3.58 | 3.92 | 2.44 |
| Detergent[c] | 3.41 | 3.54 | 4.28 |
| Non-ionic Detergent[d] | 2.76 | 2.92 | 3.18 |

[a]Hydrolysis of Soman is followed by measuring the fluoride released with the ion specific electrode. The activity was measured as μ moles of fluoride released/-minute/mg of enzyme.
[b]Alkali, Laundry CID-A-A-876, General Services Administration, Washington, D.C. (1980).
[c]Laundry Detergent Type II, Federal Specification, Detergent, Laundry and Hand Washing (Granular), P-D-245E.
[d]Non-ionic Detergent Type I, Military Specification, Detergent, General Purpose (Liquid, Nonionic), MIL-D-16791F.

Other conditions of the experiments were the same as those given above. The enzyme activity with Alkali or with the laundry detergent type II was increased two fold when the temperature of the reaction mixture was increased from 30° C. to 40° C. at pHs 8.5 and 9.5.

EXAMPLE 19

Detoxification of Soman with *E. coli* Enzyme—Detergent at Different pHs

Table 10 below gives the results obtained for the detoxification of soman using the *E. coli* enzyme extract with the detergent formulations at pH 7.0 and pH 9.5 at 40° C. incubation for 10 minutes (Ellman, G. L., Courtney, K. D., Andres, V. Jr., and Featherstone, R. M., "A New Rapid Determination of Acetylcholinesterase Activity" Biochem. Pharmacol. 7:88–95 (1961)).

The reaction mixture was diluted after the 10 minutes of incubation and the toxic fraction of soman that had not been hydrolyzed was quantitated by the Ellman reaction using eel acetyl cholinesterase enzyme inhibition.

The fluoride released from the agent by hydrolysis was monitored with the fluoride specific electrode during the incubation of the enzyme detergent formulation with the agent and also during the quantitation of toxic fractions of soman by acetylcholinesterase enzyme inhibition. The detoxification of soman was increased by the increase in pH from 7.0 to 9.5. Also the detoxification is increased by the presence of manganese salt in the reaction mixture. This data are provided in Table 10 below.

TABLE 10

Hydrolysis and Detoxification of Soman by *E. coli* Extract[a]

| | Percent Hydrolysis | Percent Detoxification |
|---|---|---|
| I. pH 7.0 | | |
| Detergent[d] | 2.6 | 3.3 |
| Detergent + Mn$^{++}$ | 4.0 | 8.7 |
| Detergent + Enz. Ext.[c] | 25.3 | 16.7 |
| Detergent + Enz. Ext. + Mn$^{++}$ | 50.0 | 22.7 |
| II. pH 9.5 | | |
| Alkali[b] | 22.2 | 33.4 |
| Alkali + Mn$^{++}$ | 17.6 | 34.0 |
| Alkali + Enz. Ext.[c] | 22.1 | 28.1 |
| Alkali + Enz. Ext. + Mn$^{++}$ | 48.2 | 40.0 |
| Detergent[d] | 12.9 | 21.1 |
| Detergent + Mn$^{++}$ | 17.5 | 21.1 |
| Detergent + Enz. Ext.[c] | 31.2 | 35.4 |
| Detergent + Enz. Ext. + Mn$^{++}$ | 44.7 | 40.8 |

[a]Hydrolysis of Soman is followed by measuring the fluoride released with the ion specific electrode at 40° C. Detoxification of Soman was determined by measuring the inhibition of eel acetylcholinesterase enzyme.
[b]Alkali.
[c]0.3 mL *E. coli* enzyme extract.
[d]Laundry Detergent, Type II.

EXAMPLE 20

Enzyme Activity

The temperature optimum for the *E. coli* enzyme was 45° C., above which the enzyme was rapidly inactivated. It is, therefore important that the enzyme detergent formulation be used at 45° C. or below for activity. However, the incorporation of similar enzyme extracts from thermophilous organisms such as *Bacillus Sterothermophilus* may provide higher temperature stability. The net hydrolytic activity of the *E. coli* enzyme increased with an increase in pH up to 9.5, with both DFP and soman as the substrates, indicating the beneficial effect of the enzyme from *E. coli* in the detergent formulation. The pH optimum studies using bis pNPP (see, FIG. 2) also indicated a second pH optimum for this enzyme on the alkaline side.

The studies demonstrated an increase in catalytic activity of the enzyme in the presence of alkali and laundry detergent type II as pHs 8.5 and 9.5. These pHs values not only increase the catalytic hydrolysis of the agent, but also increase the detergent of the laundry formulation in removing soil from clothing and other articles.

Moreover, pH 9.5 represents fairly mild conditions compared with standard chemical decontaminating solutions currently used and thus could be used on a number of surfaces or conditions for decontamination along with cleaning. The *E. coli* enzyme is quite stable when stored at 4° C. and retains its full catalytic activity for more than one year. The enzyme solution could also be freeze dried without any loss of activity.

A detergent formulation based on alkali, linear alkyl sulfonate, citric acid and freeze dried *E. coli* extract had the same DFPase activity as the enzyme extract with detergent formulation at pH 9.5. The neutrase enzyme from Novo Laboratories looks good for use in place of *E. coli* enzyme, even though the hydrolysis and detoxification of soman was not significant with the conditions used in this study.

A recent report by Attaway et al has demonstrated DFP hydrolyzing and detoxifying activities with a number of bacterial cell free extracts (including from *E. coli* ATCC 25922) and acetone powder preparations (Attaway, H., Nelson, J. O., Baya, A. M., Voll, M. A., White, W. E., Grimes, D. J., and Colwell, R. R., "Bacterial Detoxification of Diisopropyl Fluorophosphate" Appl. and Environ. Microbiol. 53:1685-1689 (1987)).

The DFPase activities were determined in a buffer medium and the activity reported as comparable to the activity reported here with a buffer system and given in Table 2 above. However, the hydrolytic activity of the *E. coli* enzyme extract against DFP was significantly higher in the detergent formulations at pH 9.5 (see, Table 2).

Earlier studies reported by Hoskin et al. showed that the *E. coli* (ATCC 25922) enzyme hydrolyzed soman but did not detoxify the agent (Hoskin, F. C. G., Chettur, G., Gallo, B. J., Robbins, F. M., and Walker, J. E., "Hydrolysis and Detoxification of Soman and Dimebu by Microbial and Squid DFP-ases" Proceedings of the 1986 U.S. Army Chemical Research, Development and Engineering Center Scientific Conference on Chemical Defense, pp 283-288 (1987)).

Hoskin et al used partially purified enzyme (using cold ethanol precipitation) followed by immobilization of the enzyme on agarose resin. This enzyme-agarose complex was used for detoxification studies. The results of the present studies (see, Table 10) using crude *E. coli* enzyme extract in the presence of laundry detergent type II show that detoxification was 45% of the total soman being hydrolyzed at pH 7.0, while detoxification was 91% of the total soman hydrolyzed at pH 9.5.

Hydrolysis and detoxification of soman by the *E. coli* enzyme in the presence of alkali were comparable to the results obtained with laundry detergent type II. It is interesting to note that Soman was detoxified at a higher rate than hydrolysis (i.e., fluorine release) in the presence of alkali.

These hydrolysis and detoxification studies clearly indicate the synergistic effect of soman detoxification in the presence of alkali. It is possible that soman is detoxified in the presence of alkali by a mechanism other than by fluorine removal, such as the cleavage of pinacolyl alcohol (1,2,2-trimethylpropyl alcohol) from soman. One of the end products of this reaction would be methylfluorophosphonate, and this compound is not detected by the fluoride specific electrode. Moreover, there is no information in the literature to indicate that methylfluorophosphonate is inhibitory to the eel acetylcholinesterase enzyme used for the detoxification studies of soman.

Enzymes isolated from non-sporulating rod like obligate thermophiles (JD 100 and JD 300) have been shown to have catalytic activities against soman, both hydrolysis and detoxification. The enzymes from these thermophiles which have a high temperature optimum (stability and activity) against G-agents can also be incorporated into the enzyme detergent formulation described herein and the laundry operation can be carried out at high temperatures for complete detoxification of G-agents (Hoskin, F. C. G., Chettur, G., Gallo, B. J., Robbins, F. M., and Walker, J. E., "Hydrolysis and Detoxification of Soman and Dimebu by Microbial and Squid DFP-ases" Proceedings of the 1986 U.S. Army Chemical Research, Development and Engineering Center Scientific Conference on Chemical Defense, pp 283-288 (1987); DeFrank, J. J., "Thermostable Bacterial Enzymer for Organophosphorus Agent Detection/Decontamination" Proceedings of the 1986 U.S. Army Chemical Research, Development and Engineering Center Scientific Conference on Chemical Defense, pp 635–641 (1987)).

EXAMPLE 21

Addition of Iodosobenzoate

Iodosobenzoate was evaluated in this study for chemical decontamination of OPA chemicals in order to generate comparative data for the non-enzymatic approach to decontamination. Iodosobenzoate was tested against DFP and soman and was shown to be catalytically active against the agents in a detergent formulation.

Iodosobenzoate was more active at pH 9.5 than at lower pHs. Hydrolysis and detoxification studies of soman by iodosobenzoate in the presence of alkali clearly indicate that there was almost 100% detoxification of total soman hydrolysed. Iodosobenzoate was also active against DFP in the presence of sea water.

The catalytic degradation of soman by iodosobenzoate in the presence of sea water has to be studied at different temperatures and conditions before its potential use for decontamination of G-agents can be fully assessed, including possible Nave application in the present of sea water.

EXAMPLE 22

Chemical Decontaminating Laundry Detergent Formulation

Enzymes are routinely incorporated in commercial laundry detergent formulations. The primary purpose of this study is to improve cleaning under mild laundry conditions by the use of proteases or lipases for the removal of protein/lipid bound stains and/or soils. We have demonstrated that an OPA chemical degrading enzyme from *E. coli* can be incorporated into a detergent formulation with successful decontaminating activity. This decontaminating activity was demonstrated at neutral to alkaline pHs. The incorporation of a laundry detergent type II and *E. coli* enzyme into a formulation at the concentrations evaluated in this study will produce the hydrolysis and detoxification of soman as follows.

If soman were present in contaminated clothing at 2 g per square meter (g/m$^2$) then 82% would be hydrolyzed and 74.6% detoxified in 33 minutes (see, Tables 11 and 12 below).

If soman were present at 10 g/m$^2$ of clothing, then 16.4% would be hydrolyzed and 14.95 would be detoxified in 33 minutes.

TABLE 11

Trailer Mounted Laundry for Overgarment 84[a]

| OPERATION | WATER LEVEL (inch) | TIME (min.) | TEMP. (°C.) | SUPPLIES (per 13.6 kg) |
|---|---|---|---|---|
| SUDS | 11 | 5 | 40 | 8 oz. |
| " | " | " | " | 4 oz. |
| " | " | " | " | 4 oz. |
| RINSE | " | 2 | 28.5 | — |
| " | " | " | " | — |
| " | " | " | " | — |

[a]13.6 kg (30 lbs) of Overgarment 84 were exposed with 10 g of soman per square meter. total Soman in the wash load was 258.6 g. The volume of water used per cycle was 83 liters. The volume of clothing was 38 liters. Laundry Detergent Type II[5] was used at pH 9.5 with *E. coli* enzyme extract.

TABLE 12

Rate of Hydrolysis of Soman at 40° C. in Trailer Mounted Laundry

| OPERATION | SOMAN HYDROLYZED | |
|---|---|---|
| | m MOLE | g |
| SUDS | 118 | 21.48 |
| " | 59 | 10.74 |
| " | 59 | 10.74 |
| TOTAL | | 42.42 |
| PERCENTAGE OF | 16.4% | 10 g/m$^2$ |
| SOMAN HYDROLYZED | 82.0% | 2 g/m$^2$ |

This does not consider the fact that with purification of the enzyme, increased concentration of the enzyme in the detergent formulation and/or with increased laundry time, this hydrolysis and detoxification can be increased significantly. The data contained in these two Tables are based on extrapolations from laboratory experiments.

EXAMPLE 23

Conclusions

The catalytic activity against soman and other OPA chemicals is up to about 16-fold and greater when the enzyme detergent formulation of the invention is utilized over that observed with the detergent formulation alone at pH 9.5. Soman hydrolyzed at pH 9.5 (at 40° C.) in the enzyme detergent formulation is almost completely (91%) detoxified.

The present source of soman detoxifying enzyme, squid enzyme, is very expensive and the source is limited. The *E. coli* enzyme can be produced in large quantities and be more cost effective than the squid enzyme. Another non-enzyme agent for the catalytic breakdown of soman (both hydrolysis and detoxification) is iodosobenzoic acid, which is shown in this study to be catalytically active against soman and other agents in a detergent formulation and sea water.

The invention now being fully described, it will be apparent to one of ordinary skill in the art that many changes and modifications can be made thereto without departing from the spirit or scope of the invention as said firth herein.

We claim:

1. An enzyme detergent composition capable of detoxifying warfare nerve agents and other organophosphorus acid chemicals, comprising
    a laundry detergent; and
    an enzymatic cell free extract from *E. coli* containing organophosphorous acid anhydrolase the composition having a pH of about 6.5 to 10 in water.

2. The composition of claim 1, further comprising iodosobenzoate.

3. The composition of claim 1, wherein the pH is about 7.0 to 9.5.

4. The enzyme detergent composition of claim 1, wherein
    the enzymatic cell free extract is from *E. coli* having an ATCC Accession No. 25922.

5. The composition of claim 1, further comprising a manganese compound.

6. A method of cleaning and detoxifying a product contaminated with organophosphorous chemicals, comprising
    contacting the product with an amount of an aqueous suspension of the enzyme detergent composition of claim 1 at a temperature of about 20 to 50 degrees centigrade; and
    rinsing the product.

* * * * *